(12) United States Patent
Hawken et al.

(10) Patent No.: US 11,432,946 B2
(45) Date of Patent: Sep. 6, 2022

(54) BREAST PROSTHESES

(71) Applicant: BOOST INNOVATIONS LIMITED, Calstock (GB)

(72) Inventors: Christopher John Hawken, Cornwall (GB); Samantha Jane Jackman, Calstock (GB); Rosie Brave, Plymouth (GB)

(73) Assignee: BOOST INNOVATIONS LIMITED, Cornwall (GB)

( * ) Notice: Subject to any disclaimer, the term of this patent is extended or adjusted under 35 U.S.C. 154(b) by 0 days.

(21) Appl. No.: 16/812,414

(22) Filed: Mar. 9, 2020

(65) Prior Publication Data
US 2020/0281744 A1    Sep. 10, 2020

(30) Foreign Application Priority Data
Mar. 8, 2019   (GB) ..................................... 1903173

(51) Int. Cl.
*A61F 2/52*    (2006.01)
*A41C 3/06*    (2006.01)
*A41C 3/14*    (2006.01)

(52) U.S. Cl.
CPC ............... *A61F 2/52* (2013.01); *A41C 3/065* (2013.01); *A41C 3/146* (2013.01); *A61F 2230/0063* (2013.01); *A61F 2250/0078* (2013.01)

(58) Field of Classification Search
CPC . A41C 3/065; A41C 3/146; A61F 2230/0063; A61F 2250/0078; A61F 2/52
USPC ................... 450/37, 39, 54–57; 623/7, 8
See application file for complete search history.

(56) References Cited

U.S. PATENT DOCUMENTS

| | | | |
|---|---|---|---|
| 401,028 A * | 4/1889 | Greene | |
| 3,811,133 A | 5/1974 | Harris | |
| 4,258,442 A * | 3/1981 | Eberl | A61F 2/52 450/41 |
| 4,890,608 A | 1/1990 | Steer | |
| 5,522,892 A * | 6/1996 | Lin | A41C 3/144 450/39 |
| 5,545,217 A | 8/1996 | Offray et al. | |
| D383,591 S * | 9/1997 | Hyde | D2/701 |
| 5,951,367 A * | 9/1999 | Hsu | A41C 3/144 450/57 |
| 6,338,665 B1 * | 1/2002 | Dawson | A41C 3/065 450/37 |

(Continued)

FOREIGN PATENT DOCUMENTS

| | | |
|---|---|---|
| CN | 104783924 A | 7/2015 |
| EP | 3626210 A1 | 3/2020 |

(Continued)

*Primary Examiner* — Gloria M Hale
(74) *Attorney, Agent, or Firm* — Finch & Maloney PLLC; Jay S. Franklin; Michael J. Bujold

(57) ABSTRACT

A breast prosthesis comprises a resiliently-compliant silicone shell (1;11) which has an outer wall (2;12) configured to simulate the shape of a female breast. The wall (2;12) is fretted with an ornamental pattern of perforations (6;16) that vent the internal cavity (4;14) of the shell (1;11), and ribs (5;15) within the cavity (4;14) extend across it in resiliently supporting and retaining the breast-shape of the shell (1;11). The ribs (5;15) are interconnected with one another and are molded integrally with the outer wall (2;12). The shell (1;11) has a flat peripheral rim (3;13) to the cavity (4;14).

11 Claims, 5 Drawing Sheets

(56) References Cited

U.S. PATENT DOCUMENTS

| | | | |
|---|---|---|---|
| 6,878,034 B1* | 4/2005 | Cisneros | A41C 3/04 |
| | | | 450/36 |
| 2011/0301706 A1* | 12/2011 | Brooks | A61F 2/12 |
| | | | 623/8 |
| 2013/0325119 A1* | 12/2013 | Mojaradi | A61F 2/12 |
| | | | 623/8 |
| 2014/0257481 A1* | 9/2014 | Brooks | A61F 2/12 |
| | | | 623/8 |
| 2015/0327987 A1 | 11/2015 | Schuessler et al. | |
| 2017/0189208 A1 | 7/2017 | Valdiserra et al. | |
| 2020/0085594 A1 | 3/2020 | Stelter | |

FOREIGN PATENT DOCUMENTS

| | | |
|---|---|---|
| WO | 2015197938 A1 | 12/2015 |
| WO | 2020002843 A1 | 1/2020 |
| WO | 2020087143 A1 | 5/2020 |

* cited by examiner

BREAST PROSTHESES

FIELD OF THE INVENTION

This invention relates to breast prostheses.

BACKGROUND OF THE INVENTION

After a mastectomy women often choose to wear a breast prosthesis under clothing, in order to maintain a feminine shape. The prosthesis used is often of a form in which a soft, fluid-like silicone gel is encased in a thin plastics membrane, and is held in place within one or more pockets of an adapted 'bra' (brassiere). Prostheses of this form usually have a limited life of perhaps up to two years only, and there is the ever-present danger of leakage of the gel in the event of damage or puncture of the membrane. Furthermore, there are the disadvantages that the mass of gel causes the prosthesis to be heavy and hot to the wearer, especially in circumstances of physical activity, and its weight tends to pull the supporting bra forward away from the chest of the wearer, leaving unsightly and uncomfortable gaps.

SUMMARY OF THE INVENTION

It is an object of the present invention to provide a breast prosthesis that avoids the above disadvantages.

According to one aspect of the present invention there is provided a breast prosthesis comprising a compliant shell having an outer wall which is configured to simulate the shape of a breast and which defines an internal cavity to the shell, and ribs within the cavity extending across it to maintain the shape of the shell resiliently in its breast-shape simulation.

The shell with its ribs may be a one-piece molding, and may be of a resilient silicone compound.

The outer wall of the prosthesis of the invention may be perforated to vent the internal cavity, and the perforations may together provide, or be part of, a fretted ornamental pattern of the wall.

BRIEF DESCRIPTION OF THE DRAWINGS

Two embodiments of breast prostheses according to the present invention will now be described by way of example with reference to the accompanying drawings, in which.

DETAILED DESCRIPTION OF THE PREFERRED EMBODIMENTS

Figure 1:
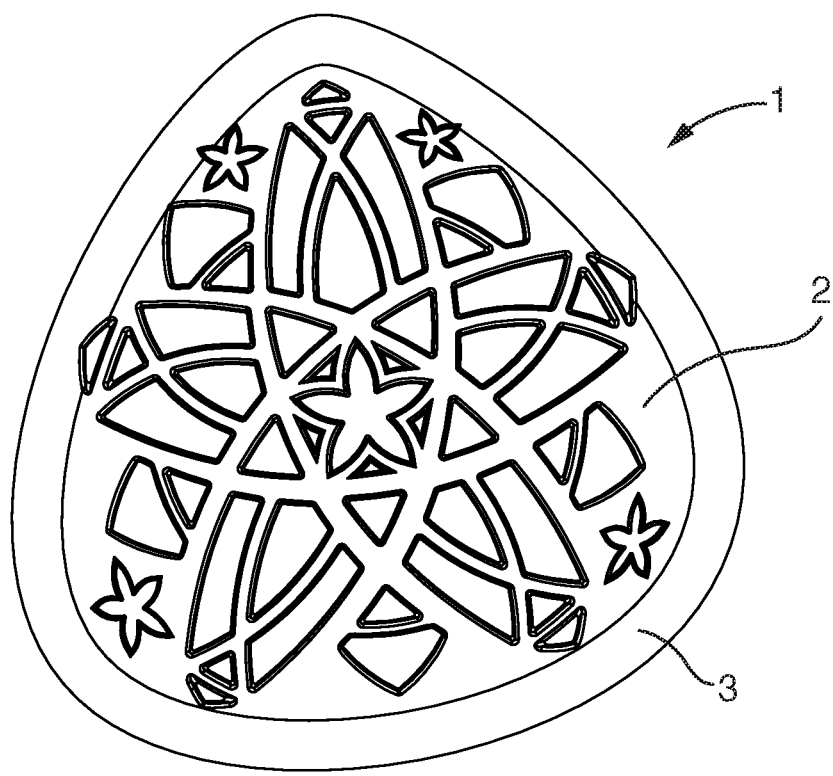
FIGS. 1 to 3 are of a first of the embodiments of breast prostheses of the invention showing it respectively in front elevation, in view from the top, and in view from the bottom.
Figure 2:
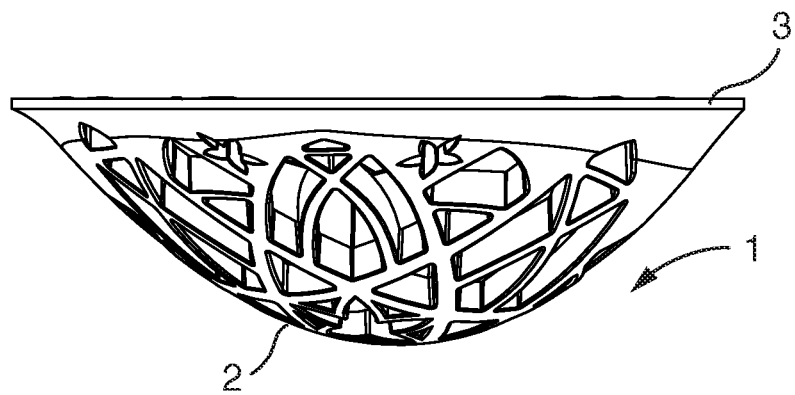
Figure 3:
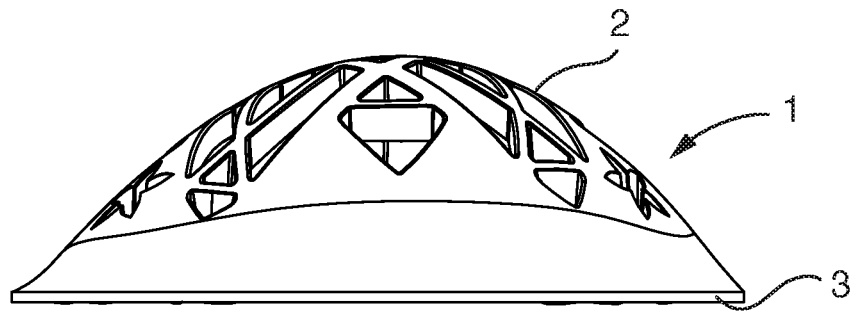
Figure 4:
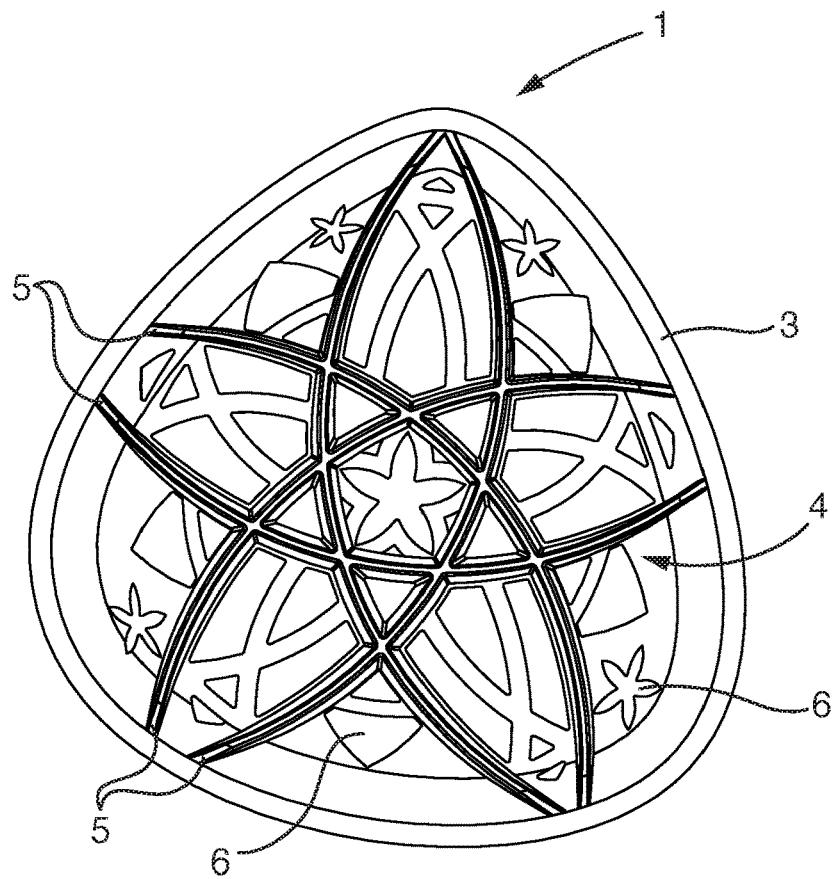
FIGS. 4 to 6 are, respectively, rear and opposite-side views of the first embodiment of breast prosthesis.
Figure 5:
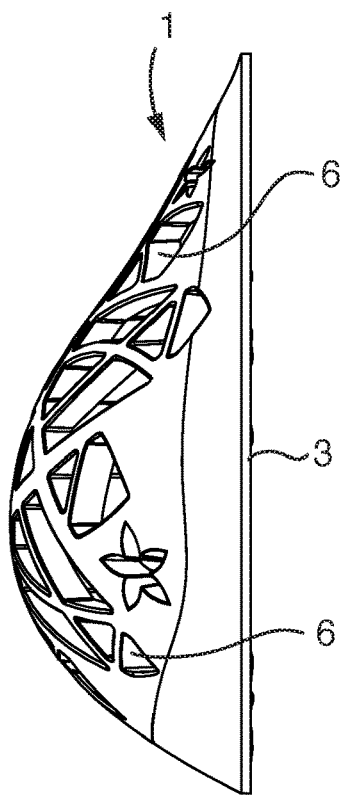
Figure 6:
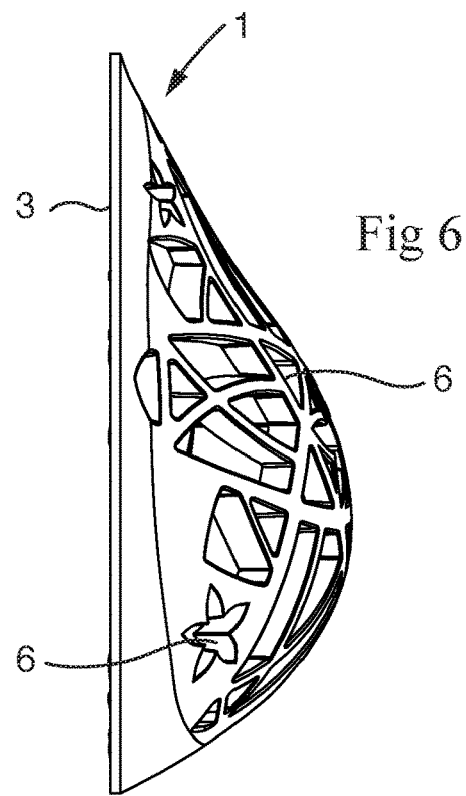
Figure 7:
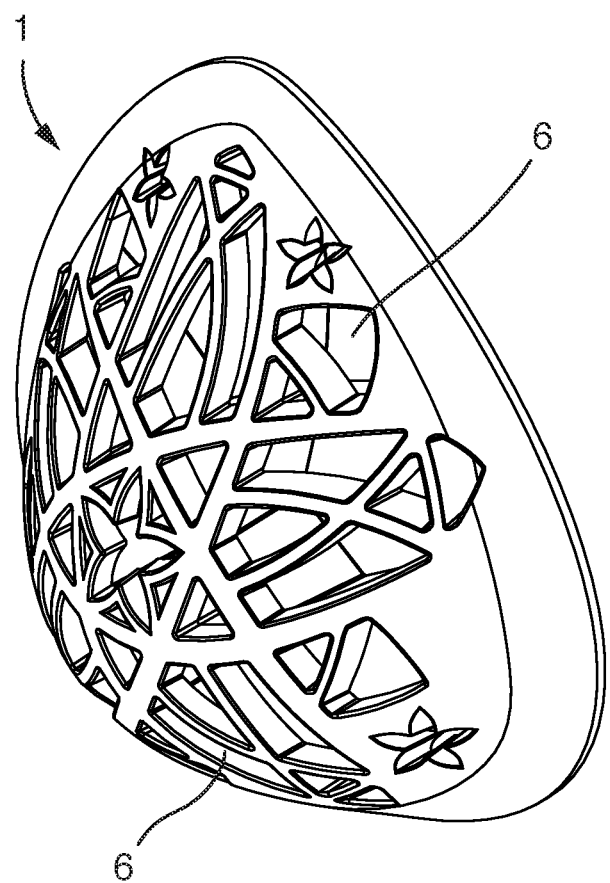
FIGS. 7 and 8 are angled views of the first embodiment of breast prosthesis from the front and rear respectively.
Figure 8:
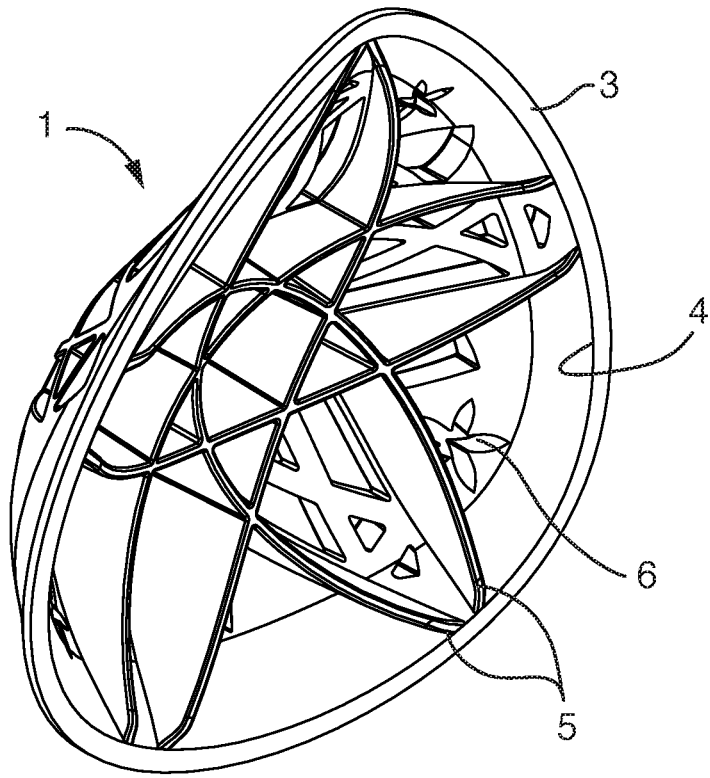

Referring to FIGS. 1 to 8, the first embodiment of the prosthesis of the invention comprises a one-piece molded shell 1 of silicone compound, having an outer wall 2 configured to simulate the shape in three-dimensional contouring of the female breast it is to replace. The shell 1 has a peripheral flat rim 3 to the cavity 4 defined by the inside, rear aspect of the outer wall 2. Ribs 5 molded integrally with the wall 2, extend across the cavity 4 to maintain resiliently the contour of the wall 2 in its simulation of the breast-shape.

The ribs 5 may be configured to give a degree of concavity into the cavity 4 in the rear aspect of the prosthesis so as to make allowance for any residual bulge of tissue or muscle resulting from the mastectomy. They may alternatively be configured with a convex form where there is concavity of the post-mastectomy scar tissue or chest wall. Furthermore, the prosthetic device of the invention may be used absent mastectomy for essentially cosmetic purposes.

The wall 2 is molded with a multiplicity of perforations 6 for venting the cavity 4. The perforations 6 are variously shaped from one to another so as to provide together a fretted ornamental pattern to the front view of the outer wall 2 of the shell 1. Moreover, the perforations 6 contribute to the compliance of the product, in that they, together with the resilient ribs 5, allow the outer wall 2 to yield to applied pressure in a way that better simulates the response of a natural breast, than is achieved with a membrane-encased mass of silicone gel.

The prosthetic shell 1 fits into the appropriate cup of a mastectomy bra (not shown), and is held in place there within pockets of the bra. The ribs 5 have a resilience that enables the shell 1 to be flexed as required to be entered in the pockets and retained there throughout wear of the bra during even significant physical activity. Moreover, the open fretted structure of the breast prosthesis described above has the advantage over known products involving a mass of membrane-encased gel, in that it is suited to use during swimming, not only because of the reduction in weight, but because water can readily pass through it.

Figure 9:
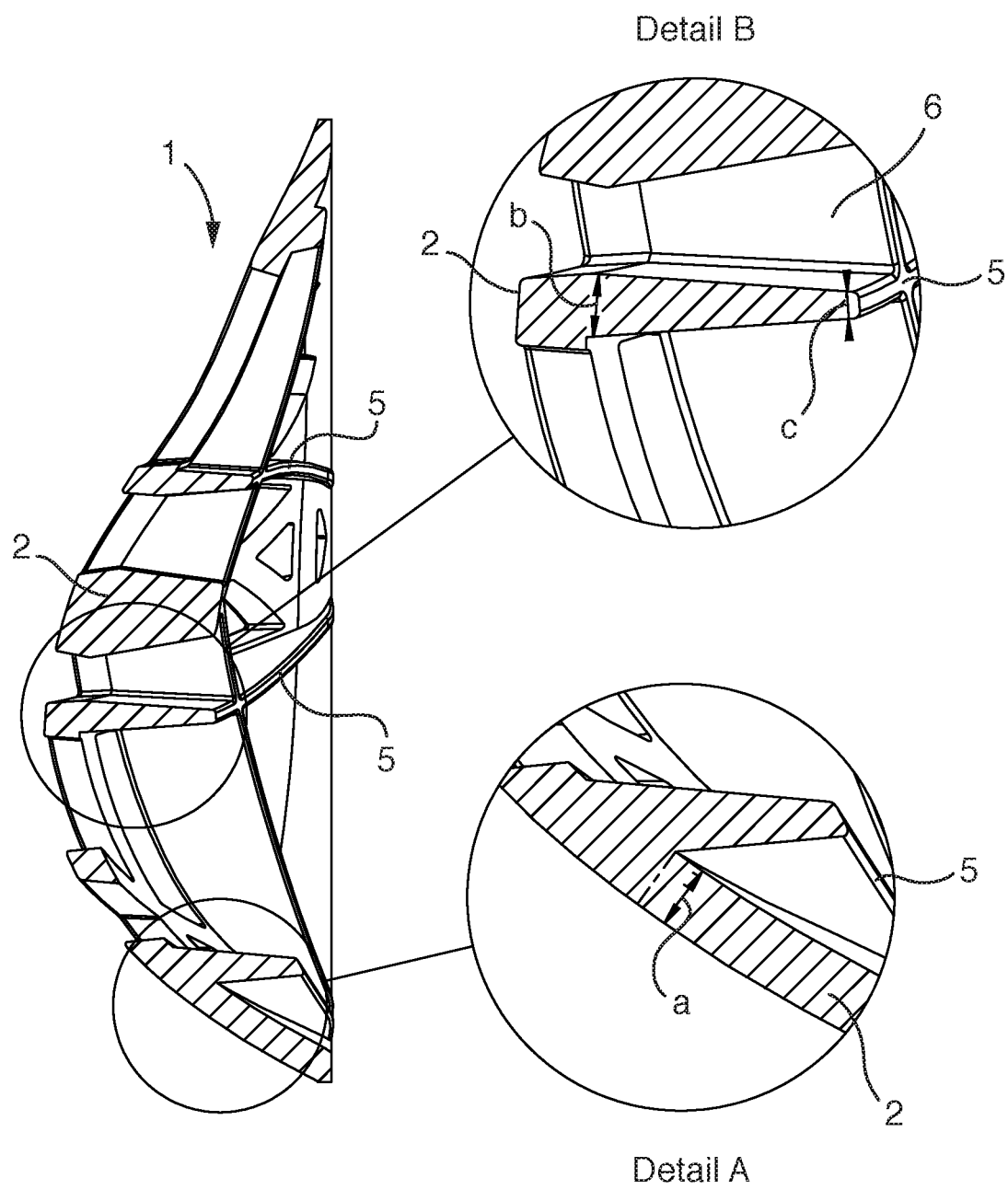
FIG. 9 is a sectional side-view of FIG. 5 showing at Details A and B enlarged sectional portions of the shell of the breast prosthesis of FIGS. 1 to 8.

FIG. 9 illustrates variation of the thickness of the material of the molding used in the example of the first embodiment of breast prosthesis. The dimension-indicating double-arrow a of Detail A indicates a thickness of the wall 2 that is comparable with the thickness at double-arrow b similarly indicated in Detail B at the entrance of a perforation 6, whereas the thickness indicated by double-arrow c deep within the same perforation 6 where merging with ribs 5 occurs, is significantly less.

Figure 10:
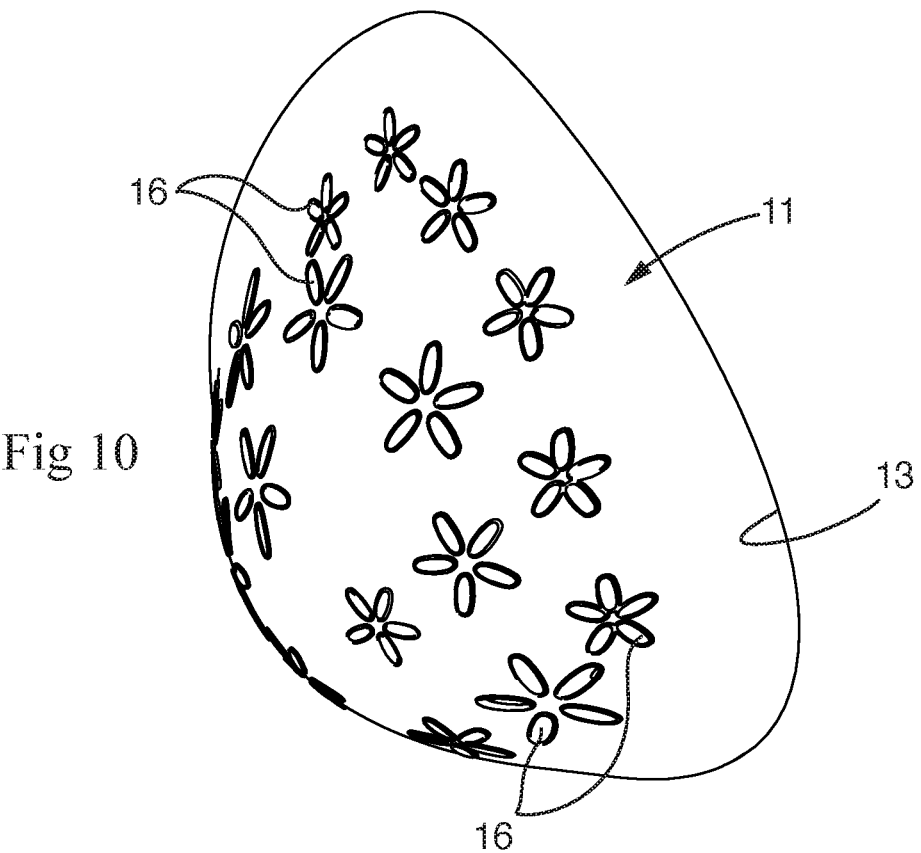
FIGS. 10 and 11 are views corresponding to those of FIGS. 7 and 8 respectively, of the second embodiment of breast prosthesis according to the invention.
Figure 11:
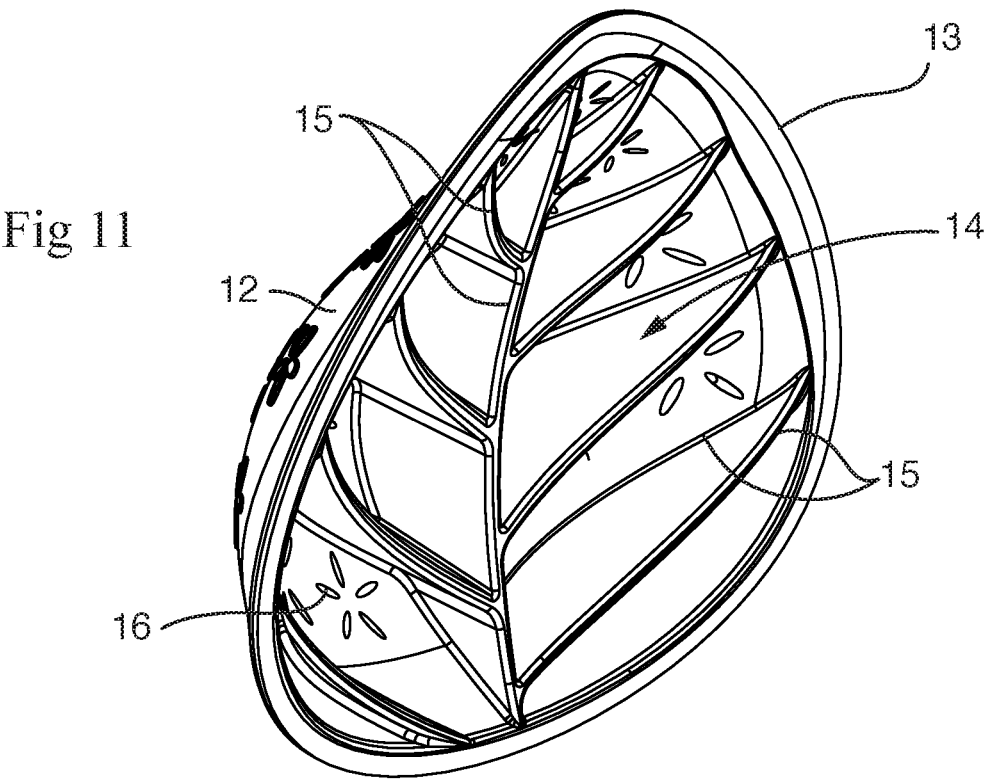

Referring to FIGS. 10 and 11, the second breast prosthesis illustrated, comprises a one-piece molded shell 11 of silicone compound having an outer wall 12 configured in overall contour and shape simulation of a breast. Like the first embodiment described above, the shell 11 has a flat rim 13 to the cavity 14 defined by the inside of the outer wall 12. However, ribs 15 molded in an interconnected network integrally with the wall 12 to provide resilient shape-support and -retention of the shell 11 in its simulation of the breast, extend in a different configuration across the cavity 14 from the configuration of the ribs 5 across the cavity 4 of the first embodiment. Also, the perforations 16 themselves and their fretted-pattern in the outer wall 12, are different from the perforations 6 and their fretted pattern of the shell 1 of FIGS. 1 to 8. This illustrates that there may be variations as between the moldings and features of breast prostheses according to the present invention, dependent on choice for structural and practical requirement, and even for cosmetic appearance.

The silicone compound used in the molding process of the breast prosthesis described, is of harder form than that used for the membrane-encased mass of silicone gel of the prior art. The molding process used according to the present invention involves additive-cure of two components of the silicone material, in which the mixing together of 'Part A' with 'Part B' in equal measures, catalyses and solidifies the material. The process comprises the steps of:

mix together the two parts of the silicone material with a pigment;

de-gas the mix in a vacuum chamber to remove bubbles;

pour the mix into the molding tool avoiding aerating it;

clamp the tool tightly closed;

after twenty minutes open the tool and remove the product;

trim any flash or other extraneous material from the product;

wash the product in a dishwasher, or otherwise in hot, soapy water;

air-dry the product; and immediately when the product is dry, pack it in a plastics bag, or preferably a soft-cotton bag.

It has been found that as so manufactured the product advantageously has a fabric-like surface texture. This avoids the usual generally-unappealing texture of molded silicone products, replacing it with a more pleasant fabric-feel.

The invention claimed is:

1. A breast prosthesis comprising: a perforated shell of resilient material having an outer wall, the outer wall having an outer surface and an inner surface and being configured to simulate the shape of a female breast, the inner surface defining an internal cavity of the shell; and a plurality of resiliently-deformable ribs, each of the ribs having an inside edge that is connected to the inner surface such that the ribs extend away from the inner surface and into the internal cavity, the ribs extending across the internal cavity to maintain the shell resiliently in the shape of the female breast, and wherein the ribs are curved when viewed from a rear aspect of the shell and are interconnected.

2. The breast prosthesis according to claim 1, wherein the shell and the ribs are a one-piece molding.

3. The breast prosthesis according to claim 1, wherein the shell and the ribs are a one-piece molding of a resilient silicone compound.

4. The breast prosthesis according to claim 1, wherein the shell has a peripheral flat rim which defines an opening to the internal cavity.

5. The breast prosthesis according to claim 1, wherein the outer wall is fretted.

6. The breast prosthesis according to claim 1, wherein the outer wall of the compliant shell is fretted with an ornamental pattern of perforations.

7. The breast prosthesis according to claim 1, wherein the ribs are shape-supporting and -retaining to the outer wall.

8. The breast prosthesis according to claim 1, wherein the ribs have an outside edge that is opposite the inside edge thereof.

9. The breast prosthesis according to claim 1, wherein a material thickness of the outside edges of the ribs is less than a material thickness of the inside edges of the ribs.

10. The breast prosthesis according to claim 4, wherein each of the ribs has an outside edge that is opposite the inside edge thereof, and the outside edge of at least one of the ribs extends laterally across the cavity from one side of the peripheral flat rim to another side of the peripheral flat rim.

11. A breast prosthesis comprising:
a perforated wall that is made of a resilient material and forms a shell, the wall has an outer surface, an inner surface and a peripheral flat rim, the wall is configured to simulate a shape of a female breast and the inner surface of the wall defines an internal cavity, the wall has a substantially consistent cross-sectional material thickness, and the flat rim defines an opening to the internal cavity;
a plurality of resiliently-deformable ribs which have an inside edge and an opposite outside edge, the inside edges of the ribs are integrally connected to the inner surface of the wall, the ribs extend from the inner surface of the wall into the internal cavity, and the outside edge of a first one of the ribs extends laterally across the internal cavity from the peripheral flat rim on one lateral side of the shell to the peripheral flat rim on an opposite lateral side of the shell, the outside edge of a second one of the ribs extends from the peripheral flat rim and intersects the outside edge of the first one of the ribs;
the cross-sectional material thickness of the wall is comparable to a cross-sectional material thickness of the inside edge of the ribs;
from a rear point of view of the breast prosthesis facing the opening, the outside edges of the ribs have curved profiles; and
the wall has a plurality of perforations to vent the internal cavity.

* * * * *